US010507121B1

(12) United States Patent
Hoffmann et al.

(10) Patent No.: US 10,507,121 B1
(45) Date of Patent: Dec. 17, 2019

(54) DEVICE AND METHOD TO DECODE VOLITIONAL MOTOR COMMANDS USING A BIOMECHANICAL MODEL FOR CONTROLLING A PROSTHETIC LIMB

(71) Applicant: HRL Laboratories, LLC, Malibu, CA (US)

(72) Inventors: Heiko Hoffmann, Simi Valley, CA (US); Vincent De Sapio, Westlake Village, CA (US); Darren J. Earl, Pasadena, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/295,762

(22) Filed: Oct. 17, 2016

Related U.S. Application Data

(60) Provisional application No. 62/242,259, filed on Oct. 15, 2015.

(51) Int. Cl.
| | |
|---|---|
| *G06F 19/00* | (2018.01) |
| *A61F 2/72* | (2006.01) |
| *G16H 50/20* | (2018.01) |
| *A61F 2/70* | (2006.01) |
| *A61F 2/76* | (2006.01) |

(52) U.S. Cl.
CPC .............. *A61F 2/72* (2013.01); *G16H 50/20* (2018.01); *A61F 2002/704* (2013.01); *A61F 2002/7635* (2013.01); *A61F 2002/7645* (2013.01)

(58) Field of Classification Search
CPC ........ B25J 9/1694; B25J 9/1628–1653; G05B 2219/40324; G05B 2219/40309; G05B 2219/40311; G05B 2219/40323; B62D 57/00–04; B62D 57/032
USPC ................ 700/245, 246, 251, 253, 260, 261
See application file for complete search history.

(56) References Cited

U.S. PATENT DOCUMENTS

| | | | | |
|---|---|---|---|---|
| 9,221,177 B2 * | 12/2015 | Herr | ..................... | B62D 57/032 |
| 2004/0186718 A1 * | 9/2004 | Nefian | ................. | G06K 9/6293 |
| | | | | 704/256 |
| 2013/0274894 A1 * | 10/2013 | Goldfarb | .................. | A61F 2/60 |
| | | | | 623/24 |

(Continued)

OTHER PUBLICATIONS

Balbinot, A., Júnior, A. S., & Favieiro, G. W. Decoding Arm Movements by Myoelectric Signal and Artificial Neural Networks. Intelligent Control & Automation (2153-0653), 4(1), 2013, pp. 87-93.

(Continued)

*Primary Examiner* — Hsien Ming Lee
(74) *Attorney, Agent, or Firm* — Tope-McKay & Associates

(57) ABSTRACT

Described is a system for decoding recorded signals into movement commands of a prosthetic device. Using a biomechanical model and physical action data, biological signal data is related to kinetic data. The physical action data can include position, joint angle, speed, and acceleration of a part of a limb. The biological signal data can include recorded neural signals and recorded muscle signals. The kinetic data can include force, power, torque, and stress. Based on the relationship between the biological signal data and the kinetic data, control commands are generated to achieve an intended position and/or movement of a prosthesis.

17 Claims, 6 Drawing Sheets

(56) References Cited

U.S. PATENT DOCUMENTS

2014/0031952 A1* 1/2014 Harshbarger ............ A61F 2/54 623/25

OTHER PUBLICATIONS

Delp SL, Anderson FC, Arnold AS, Loan P, Habib A, John CT, Guendelman E, Thelen DG. OpenSim: Open-source Software to Create and Analyze Dynamic Simulations of Movement. IEEE Transactions on Biomedical Engineering, vol. 54, No. 11, Nov. 2007, pp. 940-950.

V. De Sapio. An approach for goal-oriented neuromuscular control of digital humans in physics-based simulations. International Journal of Human Factors Modeling and Simulation, 4(2), pp. 121-144, 2014.

Momen, K., Krishnan, S., & Chau, T. Real-time classification of forearm electromyographic signals corresponding to user-selected intentional movements for multifunction prosthesis control. IEEE Transactions on Neural Systems and Rehabilitation Engineering, 15(4), pp. 535-542, 2007.

Pulliam, C. L., Lambrecht, J. M., & Kirsch, R. F. Continuous and Simultaneous Emg-Based Neural Network Control Of Transradial Prostheses. Proceedings of the 2011 MyoElectric Controls/Powered Prosthetics Symposium, 2011, pp. 1-3.

Tenore, F., Ramos, A., Fahmy, A., Acharya, S., Etienne-Cummings, R., & Thakor, N. V. Towards the control of individual fingers of a prosthetic hand using surface EMG signals. In Engineering in Medicine and Biology Society, 2007. EMBS 2007. 29th Annual International Conference of the IEEE, pp. 6145-6148.

Thelen, D. G., Anderson, F. C., & Delp, S. L. Generating dynamic simulations of movement using computed muscle control. Journal of Biomechanics, 36(3), pp. 321-328, 2003.

D.G. Thelen and F.C. Anderson. Using computed muscle control to generate forward dynamic simulations of human walking from experimental data. Journal of Biomechanics, 39(6), pp. 1107-1115, 2006.

Byron M. Yu, Gopal Santhanam, Maneesh Sahani, and Krishna V. Shenoy. Neural Decoding for Motor and Communication Prostheses. Chapter in Statistical Signal Processing for Neuroscience, K.G. Oweiss editor. Elsevier. pp. 219-263, 2010.

* cited by examiner

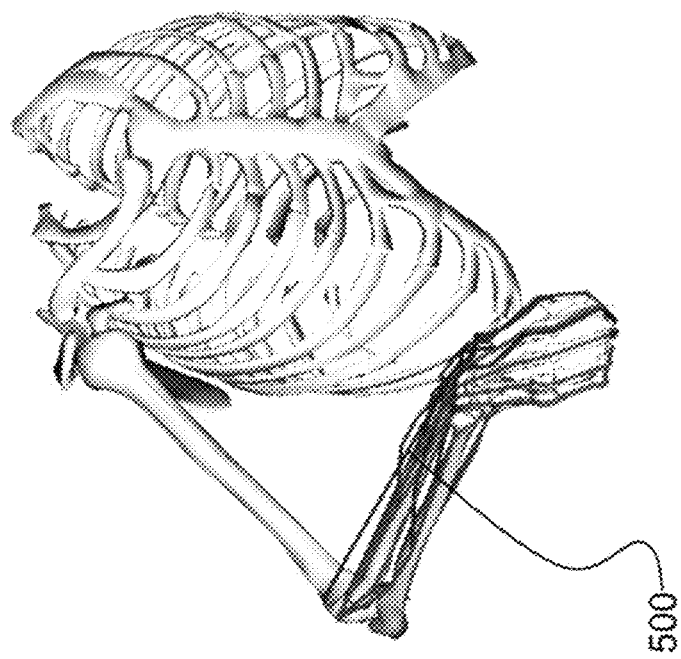

DEVICE AND METHOD TO DECODE VOLITIONAL MOTOR COMMANDS USING A BIOMECHANICAL MODEL FOR CONTROLLING A PROSTHETIC LIMB

CROSS-REFERENCE TO RELATED APPLICATIONS

This is a Non-Provisional application of U.S. Provisional Application No. 62/242,259, filed in the United States on Oct. 15, 2015, entitled, "Device and Method to Decode Volitional Motor Commands Using a Biomechanical Model for Controlling a Prosthetic Limb," which is incorporated herein by reference in its entirety.

BACKGROUND OF INVENTION

(1) Field of Invention

The present invention relates to a system for decoding volitional human motor commands into machine commands for controlling a prosthetic limb and, more particularly, to a system for decoding volitional human motor commands into machine commands using a biomechanical model of the missing limb.

(2) Description of Related Art

A prosthesis is an artificial device that replaces a missing body part (typically a limb), which may be lost through trauma, disease, or congenital conditions. The prior art for detecting volitional motor movements from residual muscle activity uses a predefined threshold on muscle signals (measured using electromyography, for example) to trigger prosthetic actuation. This technique misses useful information hidden in sub-threshold signals of other muscles.

The prior art for decoding cortical neural signals onto prosthetic movement uses a Kalman filter to map the neural population activity onto a trajectory (see Literature Reference No. 9 of the List of Incorporated Literature References). The disadvantage of this approach is that it uses a linear mapping between neural activity and prosthetic movement and is, therefore, limited in dexterity and the number of degrees-of-freedom that can be controlled simultaneously.

A straightforward extrapolation of the prior art leads to the need for accurate non-linear mappings between neural activity and prosthetic movement. However, such mappings are still unknown and too complex to be just learned from data. Thus, a continuing need exists for a system to improve the precision and dexterity of a prosthetic limb.

SUMMARY OF INVENTION

The present invention relates to a system for decoding volitional human motor commands into machine commands for controlling a prosthetic limb and, more particularly, to a system for decoding volitional human motor commands into machine commands using a biomechanical model of the missing limb. The system uses a biomechanical model and physical action data to relate biological signal data to kinetic data. The physical action data includes at least one of position, joint angle, speed, and acceleration of at least part of a limb. The biological signal data includes at least one of recorded neural signals and recorded muscle signals. The kinetic data includes at least one of force, power, torque, and stress. Based on the relationship between the biological signal data and the kinetic data, control commands are generated to achieve at least one of an intended position and movement of a prosthesis.

In another aspect, the biomechanical model is used for prediction of muscle activity related to movement of a missing limb.

In another aspect, the system uses an output of a biomechanical simulation to determine control commands.

In another aspect, a biomechanical simulation provides training data for a machine learning method that maps a set of recorded muscle signals onto control commands of the prosthetic limb.

In another aspect, the biomechanical model of a missing limb constrains the control commands to those that are biomechanically feasible within the biomechanical model.

In another aspect, the biomechanical model is personalized for an individual user having a prosthetic limb.

As can be appreciated by one skilled in the art, in another aspect, the present invention also comprises a method for causing a processor to perform the operations described herein.

Finally, in another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 5 is an illustration of muscles used in a test simulation according to embodiments of the present disclosure;

DETAILED DESCRIPTION

Figure 1:
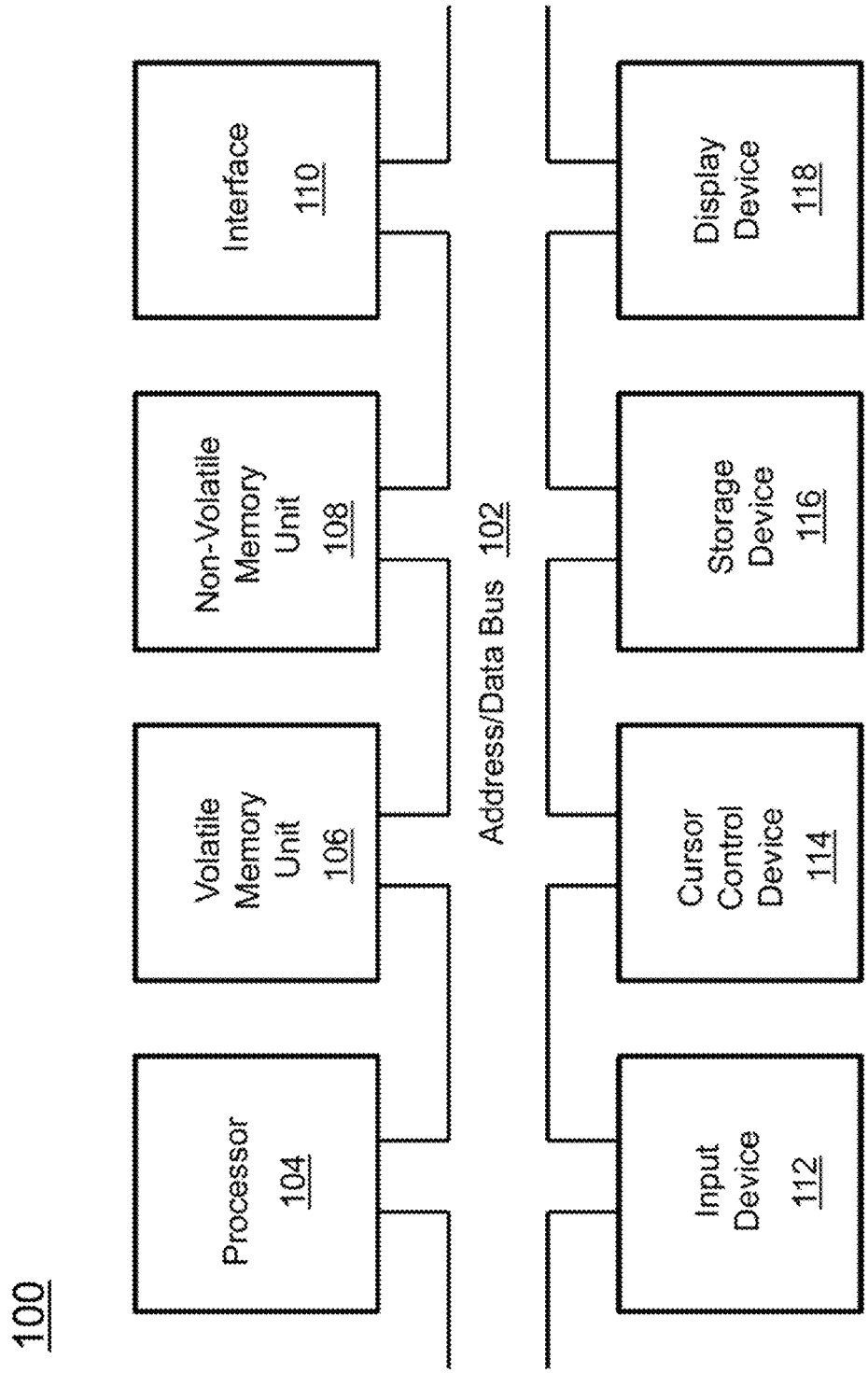
FIG. 1 is a block diagram depicting the components of a system for decoding volitional human motor commands according to embodiments of the present disclosure.

The present invention is a system for decoding volitional human motor commands into machine commands for controlling a prosthetic limb and, more particularly, to a system for decoding volitional human motor commands into machine commands using a biomechanical model of the missing limb.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number as follows:
1. Balbinot, A., Júnior, A. S., & Favieiro, G. W. Decoding Arm Movements by Myoelectric Signal and Artificial Neural Networks. Intelligent Control & Automation (2153-0653), 4(1), 2013.
2. Delp S L, Anderson F C, Arnold A S, Loan P, Habib A, John C T, Guendelman E, Thelen D G. OpenSim: Open-source Software to Create and Analyze Dynamic Simulations of Movement. IEEE Transactions on Biomedical Engineering, 2007.
3. V. De Sapio. An approach for goal-oriented neuromuscular control of digital humans in physics-based simulations. International Journal of Human Factors Modeling and Simulation, 4(2), 121-144, 2014.
4. Momen, K., Krishnan, S., & Chau, T. Real-time classification of forearm electromyographic signals corresponding to user-selected intentional movements for multifunction prosthesis control. IEEE Transactions on Neural Systems and Rehabilitation Engineering, 15(4), 535-542, 2007.
5. Pulliam, C. L., Lambrecht, J. M., & Kirsch, R. F. Continuous and Simultaneous Emg-Based Neural Network Control Of Transradial Prostheses. Proceedings of the 2011 MyoElectric Controls/Powered Prosthetics Symposium, 2011.
6. Tenore, F., Ramos, A., Fahmy, A., Acharya, S., Etienne-Cummings, R., & Thakor, N. V. Towards the control of individual fingers of a prosthetic hand using surface EMG signals. In Engineering in Medicine and Biology Society, 2007. EMBS 2007.29th Annual International Conference of the IEEE (pp. 6145-6148). IEEE, 2007.
7. Thelen, D. G., Anderson, F. C., & Delp, S. L. Generating dynamic simulations of movement using computed muscle control. Journal of Biomechanics, 36(3), 321-328, 2003.
8. D. G. Thelen and F. C. Anderson. Using computed muscle control to generate forward dynamic simulations of human walking from experimental data. Journal of Biomechanics, 39(6), 1107-1115, 2006.
9. Byron M. Yu, Gopal Santhanam, Maneesh Sahani, and Krishna V. Shenoy. Neural Decoding for Motor and Communication Prostheses. Chapter in Statistical Signal Processing for Neuroscience, K. G. Oweiss editor. Elsevier. 219-263, 2010.

(2) Principal Aspects

Various embodiments of the invention include three "principal" aspects. The first is a system for decoding volitional human motor commands. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
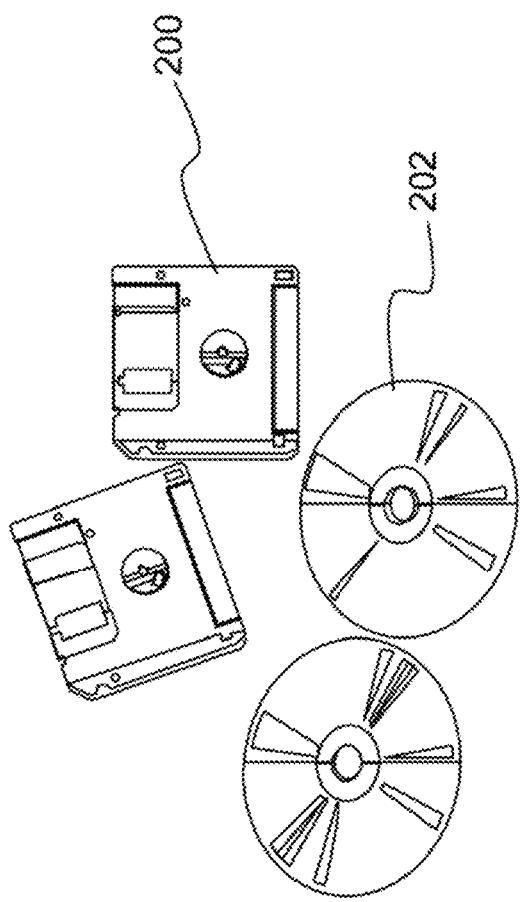
FIG. 2 is an illustration of a computer program product according to embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is a system to decode volitional human motor commands into machine commands for controlling a prosthetic limb. Machine commands are applied by an actuator connected with the prosthetic limb. The actuator is a component of a machine that is responsible for moving or controlling a mechanism or system, in this case, a prosthesis. An actuator requires a control signal (e.g., electric voltage, current, pneumatic pressure, hydraulic pressure) and a source of energy (e.g., electric current, hydraulic fluid pressure, pneumatic pressure). When the control signal is received, the actuator responds by converting the energy into mechanical motion of the prosthetic limb, such as movement of an arm, hand, leg, foot, fingers, and toes.

The system uses a biomechanical model of the missing limb to constrain the possible muscle commands to those biomechanically feasible within the model and, thereby, improve the accuracy and reliability of the decoding mechanisms. The model is used to map the muscle signals onto intended prosthesis movements. Given data generated by the model, function approximation is used to enable fast decoding and adaptation to the patient's physiology and amputation.

In an embodiment of the system described herein, the purpose is to improve the precision and dexterity of a prosthetic limb. The prior art is limited to controlling at most three, but often only one, degree-of-freedom at a time. This restriction arises from the challenge of recording accurately from motor axons/muscles and mapping the result onto prosthetic movements. For example, a single motor axon may affect multiple muscles, and a muscle can affect multiple finger joints (i.e., bones). Moreover, the recorded motor signals are noisy and incomplete.

The present invention uses a biomechanical model to predict muscle activity related to the movement repertoire of the missing limb and uses this activity to constrain the estimated intended muscle activity of the user. Only within recent years have biomechanical models become sufficiently accurate to enable predictions, such as for movement disorders, tendon surgery, and the design of manufacturing processes. Research in these areas is still very active (see, for example, Literature Reference No. 3), and experts in the technical field still disagree about details of biomechanical models and their relevance.

Figure 3:
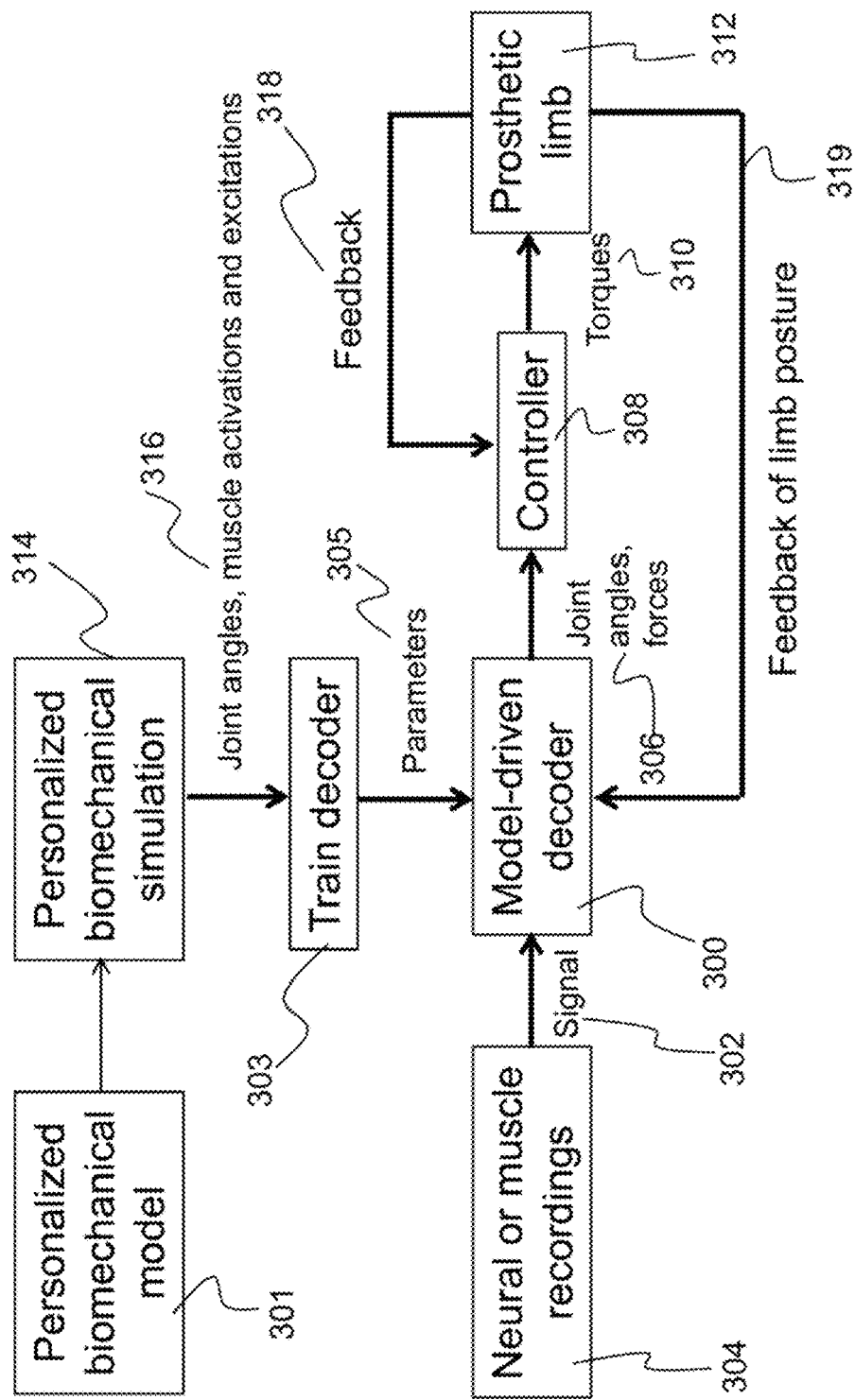
FIG. 3 is a flow chart depicting decoding volitional human motor command according to embodiments of the present disclosure.

FIG. 3 shows some of the elements and the process flow of the invention described herein. A model-driven decoder 300 (decoding processor) converts muscle and/or nerve signals 302 from neural and/or muscle recordings 304 (e.g., electromyography (EMG)) into kinetic data (e.g., joint angles and/or contact forces 306), which a controller 308 converts into motor control commands (e.g., torques 310) for a prosthetic limb 312. The controller 308 is a conventional feedback controller that tracks desired joint angles and/or contact forces (reference signals) by specifying control torques for the prosthetic arm. Sensors on the arm feedback the measured joint angles and/or contact forces, and the control loop compensates for any error between the measured and reference signals. The kinetic data includes at least one of force (i.e., interaction that will change motion of the limb), power (i.e., rate at which the limb does work), torque (i.e., twisting force of the limb), and stress (i.e., force applied to the limb) of a limb.

The decoder 300 provides the mapping between neural (EEG) or muscle (EMG) recordings and the resulting arm motion/forces (joint angles/contact forces) and is trained using the personalized musculoskeletal simulation. The decoder 300 relies on a musculoskeletal model (i.e., personalized biomechanical model 301) and a personalized biomechanical simulation 314 that can link recorded muscle signals with hand/finger movements and contact forces (i.e., joint angles and muscle activations 316). The personalized biomechanical model 301 is a data file read in and simulated by the personalized biomechanical simulation 314. A non-limiting example of software that implements such a musculoskeletal model is OpenSim software (see Literature Reference No. 2 for a description of OpenSim). This software simulates, for example, arm, hand, and finger movements, and the contact forces between fingers and environment (i.e., joint angles 316). Moreover, the software can compute the muscle activations 316 that cause the movements and contact forces. Gravity and muscle constraints are included in these computations. The muscle constraints reflect the maximum isometric force exertable by each muscle. Publically available experimental data sources are available that quantify maximum isometric force for individual muscles, in $50^{th}$ percentile male and female subjects. These data values can be scaled and personalized to a specific individual. The underlying muscle control algorithm has been demonstrated to predict muscle activation patterns based on joint-space motion trajectories (see Literature Reference Nos. 3, 7, and 8 for descriptions of the muscle control algorithm).

Initially, the model (i.e., biomechanical model 301) is personalized to the human prosthesis user by matching the user's skeletal dimensions (either by direct limb measurement or by an optical motion capture system), and by scaling existing maximum isometric force data of individual muscles for $50^{th}$ percentile male and female subjects. The detailed model of the missing limb and connecting body comprises the three-dimensional skeleton, muscle attachment points, and tendon routes. Muscle/tendon geometric properties, such as routing and attachment points to the skeleton, are publicly available based on cadaver data and imaging data. These can be scaled based on subject limb lengths. Subsequently, a large movement repertoire for the missing limb is collected and simulated with the biomechanical model 301. This movement repertoire (physical action data) includes limb movements, positions, joint angles, speed, accelerations, and forces, and the personalized biomechanical simulation 314 solves for the muscle excitations (muscle excitations result in activation and, subsequently, contraction of the muscle) that generate these actions.

For a prosthetic limb (e.g., arm), the biomechanical model 301 provides biomechanical constraints for mapping noisy and incomplete muscle signals onto hand movements/forces, acting essentially as a bio-inspired filter for motor decoding. The biomechanical constraints reflect movement and force limitations specific to the individual user. The algorithm in OpenSim (see Literature Reference No. 2) solves for a set of muscle activations (element 316) that minimize the norm of the activation vector, where the muscle activations (element 316) are associated with steady state tendon forces (i.e., tendon forces at a time when the contraction dynamics are in equilibrium and the transients have decayed). The norm of the activation vector is determined using the muscle control algorithm described above and in U.S. application Ser. No. 14/539,898, which is hereby incorporated by reference as though fully set forth herein. The steady state tendon forces must satisfy the inverse dynamics of the arm and the inequality constraints associated with the fact that muscle can generate only contractile forces.

A technical challenge for decoding is the speed of computation, which has to be below 10 milliseconds (ms). For sufficient performance, it is estimated that the control loop needs to be updated at >100 Hz (every 10 ms). This is a practical specification based on the speed of signal transmission from motor neurons to efferent muscle fibers in humans. The control loop for the prosthetic arm according to embodiments of the present disclosure should be at least as fast as the response in the human central nervous system. Since the musculoskeletal simulations (i.e., personalized biomechanical simulation 314) could not be carried out on a portable central processing unit (CPU) within this time frame, the biomechanical model 301 was used only to generate training data (i.e., train decoder 303) for a learning algorithm (i.e., model-driven decoder 300) that maps muscle signals (biological signal data) onto hand movements/forces. The biomechanical model 301 allows the generation of an exhaustive training set (i.e., train decoder 303) without burden to a human user. Non-limiting examples of learning algorithms include support vectors regression and artificial neural networks (ANNs). Multilayer, feed-forward ANNs have already been demonstrated for non-linear decoding of finger movements from surface EMG signals (see Literature Reference No. 6). ANNs have also been demonstrated for real-time classification (see Literature Reference No. 4) with high classification accuracy (i.e., 98%) (see Literature Reference Nos. 1, 5, and 6).

Figure 4:
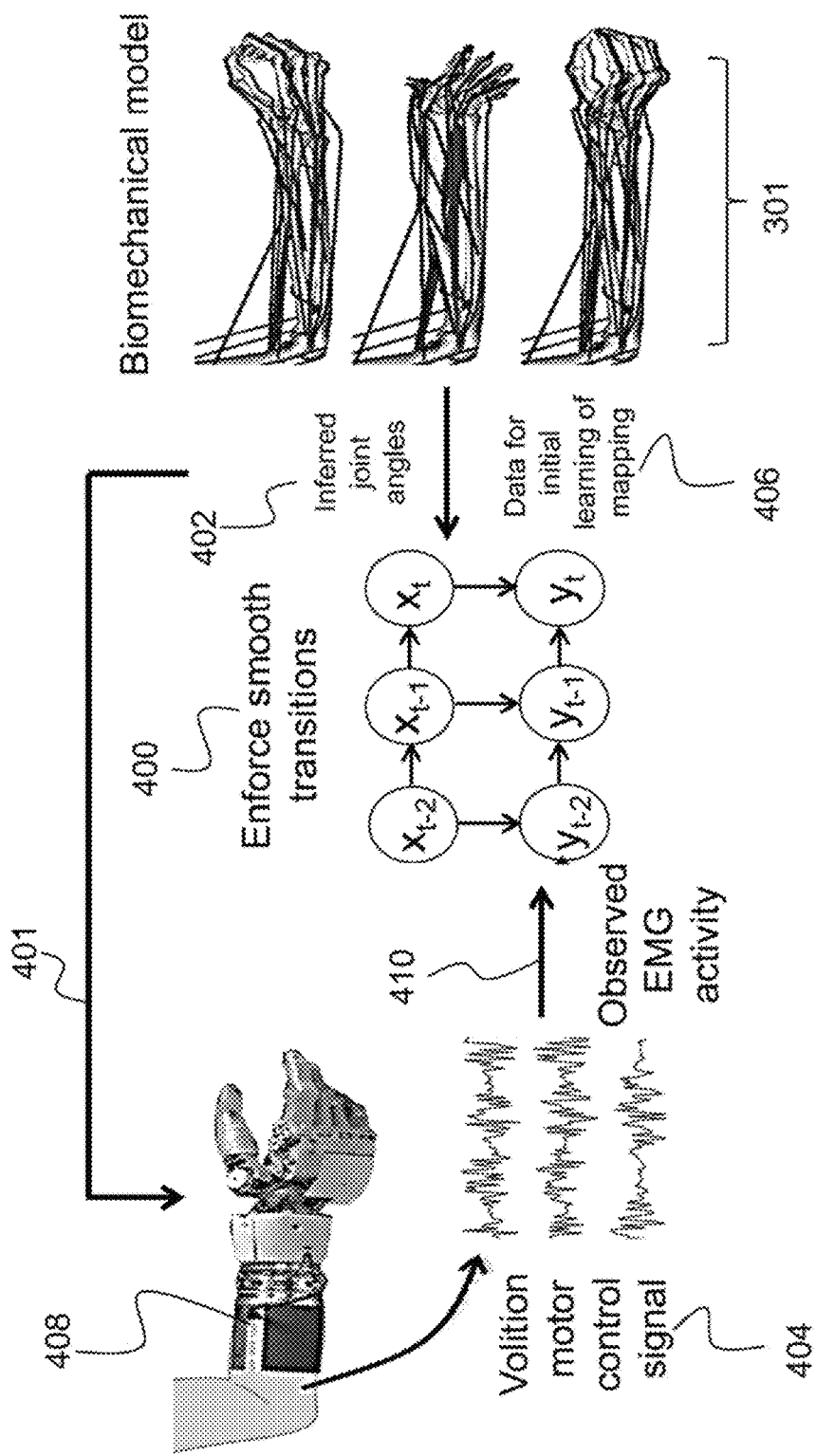
FIG. 4 is an illustration of modeling to constrain a set of plausible movements according to embodiments of the present disclosure.

To achieve continuous, smooth movements, a probabilistic approach can be used that prohibits discontinuous transitions between decoded actions and enforces smooth transitions 400, as shown in FIG. 4. A non-limiting example of an algorithm to achieve that is a Hidden Markov Model (HMM), where the hidden states are the desired actions (e.g., inferred joint angles 402) and the observables are the recorded muscle or nerve signals (e.g., observed EMG activity 410). FIG. 4 depicts using modeling (via the biomechanical model 301) to constrain the set of plausible movements and producing the movement with the highest likelihood given a recorded motor signal (e.g., observed EMG activity 410), which will be described in further detail below. The biomechanical model 301 provides the data for the mapping (i.e., data for initial learning of mapping 406) from hidden states (e.g., inferred joint angles 402) onto observables (e.g., observed EMG activity 410). For the time transitions, non-limiting examples of intervals are between 0.01 seconds and 1 second. X is a vector of joint angles, and Y is a vector of observed nerve or muscle signals (e.g., observed EMG activity 410). $x_{t-2}$, $x_{t-1}$, and $x_t$ are the states of the HMM (joint angles) at times t-2, t-1, and t. $y_{t-2}$, $y_{t-1}$, and $y_t$ are the observed nerve or muscle signals at times t-2, t-1, and t.

The biomechanical model 301 provides the data for the initial mapping (element 406) for each user. Since this mapping is learned, one can easily adapt the mapping to each user to account for individual differences in physiology. In an initial training session, the user shows his or her intended motion (i.e., volition motor control signal 404) with his or her good limb, which is tracked with an optical motion tracking system. The intended motion (i.e., volition motor control signal 404) and the corresponding muscle signals from the limb stump (i.e., observed EMG activity 410) provide new data to adapt the mapping. The arrow 401 from inferred joint angles 402 to the prosthetic hand 408 represents part of the training to learn the mapping from neural or muscle signals (i.e., biological signal data) to joint angles (elements 303 and 314 in FIG. 3).

Adaptation is also possible during use of the system according to embodiments of the present disclosure. For example, if the ANN generates a movement error associated with the volitional intent of the user (i.e., volition motor control signal 404) on a particular movement, he/she could enter a training mode (FIG. 3, train decoder 303) and manually adjust the prosthetic hand 408 to the intended configuration. A movement error can be determined by observation by the user. The user observes that the prosthetic hand 408 does not move to where he/she wants it go. The weights (or parameters 305) in the ANN will be recomputed to satisfy this new training example. The parameters 305 describe the particular learned model (e.g. weights in an ANN).

Another advantage of the model-based approach described herein is that it allows one to optimize EMG or bipolar probe placement by selecting muscles that contribute the most information to classifying the movement, while eliminating muscles that provide redundant information because of muscle synergy dependencies. A bipolar probe both senses and stimulates and is positioned over different muscles and nerves.

As depicted in FIG. 3, given the decoded desired joint angles and contact forces 306, the controller 308 implements a high-frequency (>100 Hz) control feedback loop that generates control commands (i.e., joint torques 310 to the motors in the prosthetic limb 312) using feedback 318 of prosthetic joint angle and finger-pressure sensor measurements. As part of the decoding strategy, the present invention could be combined with software assisted reflex mechanisms in the control of the prosthetic limb 312, at least initially until the user has regained natural reflexes. Feedback of limb posture 319 is the set of joint angles measures by the sensors on the prosthetic limb 312. They are fed back to the model-driven decoder 300. Those same signals are sent to the controller 308 to compensate for any error between the commanded joint angles (element 306) and the measured joint angles. In other words feedback 318 and feedback of limb posture 319 are the same signals sent to different parts of the system.

In simulation studies, the model-based decoding component (FIG. 3, element 300) of the invention was tested to demonstrate its robustness against noisy and incomplete muscle recordings and to show the advantage over the prior art thresholding approach. An idealized thresholding approach, using the best possible muscle to trigger each action, was used. Fourteen wrist movements and sixteen forces (four force vectors with four gradations each) were simulated, and all thirty actions were combined into one test set. FIG. 5 depicts the muscles 500 used in this study, specifically fifteen muscles 500 spanning the wrist. Each action resulted in a corresponding pattern of muscle activations (computed by the simulation). The study was a feasibility study to show that muscle activations could be predicted from a simulation, and accurate classifications could be made even with information from a reduced set of muscles.

Figures 6A, 6B:
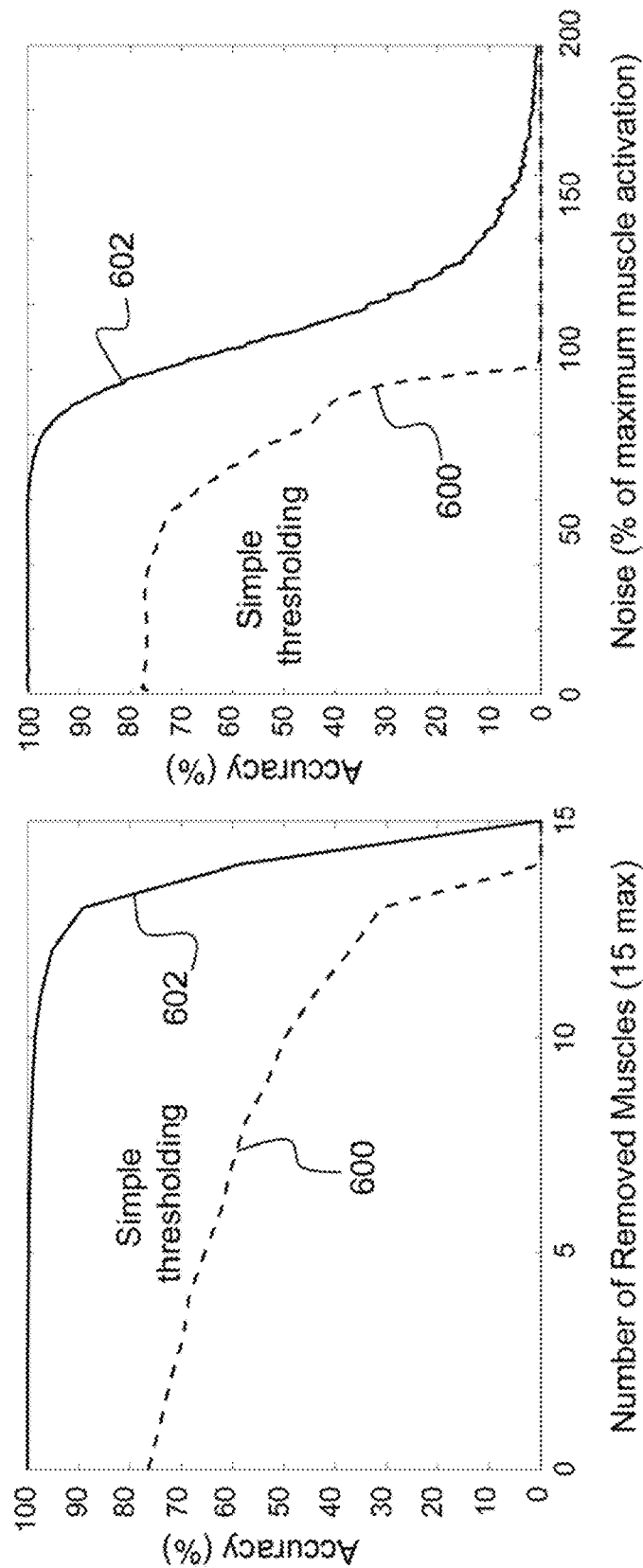
FIG. 6A is a plot illustrating a comparison of classification accuracy for actions as a function of a reduced set of recorded muscles according to embodiments of the present disclosure.
FIG. 6B is a plot illustration a comparison of classification accuracy for actions as a function of added noise according to embodiments of the present disclosure.

FIGS. 6A and 6B show the classification accuracy for predicting an action given the muscle activation. The muscle activations are a prediction of what the actual muscle activations on a biological arm would be. They are used to learn the mapping between EMG recordings to joint angles/forces that would be used to control a prosthetic limb. This accuracy is shown as a function of a reduced set of muscle activations (FIG. 6A) and as a function of added noise in the muscle activity (FIG. 6B). The significance of the reduced set of muscle activations is that it would not be possible to record all muscle activations using EMG. This demonstrates that good performance would still be achieved with a reduced number of noisy measurements. The test demonstrated dramatic improvement of motor decoding based on the biomechanical model 301 according to embodiments of the present disclosure compared with standard activity thresholding. FIG. 6A depicts classification accuracy for thirty actions (e.g., hand movement and forces) as a function of a reduced set of recorded muscles. FIG. 6B depicts classification accuracy as a function of added noise in muscle activity. For each of the plots, the y-axis is percent accuracy. The dashed lines 600 represent the simple thresholding method of the prior art, while the solid lines 602 represent the invention described herein.

The system according to embodiments of the present disclosure has applications in human performance enhancement for improving work safety in manufacturing, passenger comfort in commercial airlines, and the performance of pilots. Moreover, supporting the recovery of patients, including military veterans, who have lost limbs is another application of the present invention.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for decoding volitional motor commands for a prosthetic device, the system comprising:
   a prosthetic limb and an actuator connected with the prosthetic limb;
   a controller in connection with the prosthetic limb, wherein the controller is configured to implement a control feedback loop that specifies a joint torque for the prosthetic limb; and
   one or more processors and a non-transitory computer-readable medium having executable instructions encoded thereon such that when executed, the one or more processors perform operations of:
      using a biomechanical model and physical action data, relating biological signal data to kinetic data, the physical action data including at least one of position, joint angle, speed, and acceleration of at least part of a limb, the biological signal data including at least one of recorded neural signals and recorded muscle signals, the kinetic data including at least one of force, power, torque, and stress;
      mapping from inferred joint angles onto the biological signal data using a Hidden Markov Model (HMM);
      generating joint angle commands to achieve at least one of an intended position and movement of the prosthetic limb, wherein the biomechanical model constrains the joint angle commands to those that are biomechanically feasible within the biomechanical model;
      using the HMM to constrain the joint angle commands to be continuous; and
      sending the joint angle commands to the controller to cause the joint angle commands to be applied by the actuator connected with the prosthetic limb, wherein the actuator causes mechanical motion of the prosthetic limb based on the at least one of the intended position and movement of the prosthetic limb.

2. The system as set forth in claim 1, wherein the biomechanical model is used for prediction of muscle activity related to movement of a missing limb.

3. The system as set forth in claim 1, wherein the one or more processors further perform an operation of using an output of a biomechanical simulation to determine the joint angle commands.

4. The system as set forth in claim 1, wherein a biomechanical simulation provides training data for a machine learning method that maps a set of recorded muscle signals onto the joint angle commands.

5. The system as set forth in claim 1, wherein the biomechanical model is personalized for an individual user having the prosthetic limb.

6. The system as set forth in claim 1, wherein the prosthetic limb further comprises at least one sensor configured to provide feedback of a limb posture of the prosthetic limb in the form of a set of joint angles measured by the at least one sensor.

7. The system as set forth in claim 6, wherein the feedback of the limb posture is sent to the controller which is configured to compensate for any error between the joint angle commands and the measured set of joint angles.

8. A computer-implemented method for decoding volitional motor commands for a prosthetic device, comprising:
   an act of causing one or more processors to execute instructions stored on a non-transitory memory such that upon execution, the one or more processors perform operations of:
   using a biomechanical model and physical action data, relating biological signal data to kinetic data, the physical action data including at least one of position, joint angle, speed, and acceleration of at least part of a limb, the biological signal data including at least one of recorded neural signals and recorded muscle signals, the kinetic data including at least one of force, power, torque, and stress;
   mapping from inferred joint angles onto the biological signal data using a Hidden Markov Model (HMM);
   generating joint angle commands to achieve at least one of an intended position and movement of a prosthetic limb having an actuator connected therewith generating joint angle commands to achieve at least one of an intended position and movement of the prosthetic limb, wherein the biomechanical model constrains the joint angle commands to those that are biomechanically feasible within the biomechanical model;
   using the HMM to constrain the joint angle commands to be continuous; and
   sending the joint angle commands to a controller in connection with the prosthetic limb, wherein the controller is configured to implement a control feedback loop that specifies a joint torque for the actuator, causing the joint angle commands to be applied by the actuator connected with the prosthetic limb, wherein the actuator causes mechanical motion of the prosthetic limb based on the at least one of the intended position and movement of the prosthetic limb.

9. The method as set forth in claim 8, wherein the biomechanical model is used for prediction of muscle activity related to movement of a missing limb.

10. The method as set forth in claim 8, wherein the one or more processors further perform an operation of using an output of a biomechanical simulation to determine the joint angle commands.

11. The method as set forth in claim 8, wherein a biomechanical simulation provides training data for a machine learning method that maps a set of recorded muscle signals onto the joint angle commands.

12. The method as set forth in claim 8, wherein the biomechanical model is personalized for an individual user having the prosthetic limb.

13. A computer program product for decoding volitional motor commands for a prosthetic device, the computer program product comprising:
   computer-readable instructions stored on a non-transitory computer-readable medium that are executable by a computer having one or more processors for causing the processor to perform operations of:
   using a biomechanical model and physical action data, relating biological signal data to kinetic data, the physical action data including at least one of position, joint angle, speed, and acceleration of at least part of a limb, the biological signal data including at least one of recorded neural signals and recorded muscle signals, the kinetic data including at least one of force, power, torque, and stress;

mapping from inferred joint angles onto the biological signal data using a Hidden Markov Model (HMM);

generating joint angle commands to achieve at least one of an intended position and movement of a prosthetic limb having an actuator connected therewith generating joint angle commands to achieve at least one of an intended position and movement of the prosthetic limb, wherein the biomechanical model constrains the joint angle commands to those that are biomechanically feasible within the biomechanical model;

using the HMM to constrain the joint angle commands to be continuous; and sending the joint angle commands to a controller in connection with the prosthetic limb, wherein the controller is configured to implement a control feedback loop that specifies a joint torque for the actuator, causing the joint angle commands to be applied by the actuator connected with the prosthetic limb, wherein the actuator causes mechanical motion of the prosthetic limb based on the at least one of the intended position and movement of the prosthetic limb.

14. The computer program product as set forth in claim 13, wherein the biomechanical model is used for prediction of muscle activity related to movement of a missing limb.

15. The computer program product as set forth in claim 13, further comprising instructions for causing the one or more processors to perform an operation of using an output of a biomechanical simulation to determine the joint angle commands.

16. The computer program product as set forth in claim 13, wherein a biomechanical simulation provides training data for a machine learning method that maps a set of recorded muscle signals onto the joint angle commands.

17. The computer program product as set forth in claim 13, wherein the biomechanical model is personalized for an individual user having the prosthetic limb.

* * * * *